(12) United States Patent
Liao et al.

(10) Patent No.: US 7,829,569 B2
(45) Date of Patent: Nov. 9, 2010

(54) SOLVATE AND CRYSTALLINE FORMS OF CARBAMOYL-CYCLOHEXANE DERIVATIVES

(75) Inventors: Xiangmin Liao, Commack, NY (US); Haijian Zhu, Smithtown, NY (US); Andreas Grill, Hauppauge, NY (US)

(73) Assignee: Forest Laboratories Holdings Limited (BM)

( * ) Notice: Subject to any disclaimer, the term of this patent is extended or adjusted under 35 U.S.C. 154(b) by 243 days.

(21) Appl. No.: 12/117,972

(22) Filed: May 9, 2008

(65) Prior Publication Data

US 2009/0030007 A1    Jan. 29, 2009

Related U.S. Application Data

(60) Provisional application No. 60/917,383, filed on May 11, 2007.

(51) Int. Cl.
*A61K 31/4965*    (2006.01)
*C07D 295/00*    (2006.01)

(52) U.S. Cl. .................................. 514/255.03; 544/393
(58) Field of Classification Search ............ 514/255.03; 544/393
See application file for complete search history.

(56) References Cited

U.S. PATENT DOCUMENTS 6,566,550 B2    5/2003    Lowe, III

2006/0229297 A1*    10/2006    Csongor et al. ............. 514/218
2007/0259885 A1*    11/2007    Bathe et al. ............ 514/254.09

FOREIGN PATENT DOCUMENTS

WO    WO 2006/034774    *    4/2006
WO    WO 2007/033191 A1    3/2007

OTHER PUBLICATIONS

International Search Report for PCT/US2008/063181, mailed Aug. 15, 2008.
Written Opinion of the International Searching Authority for PCT/US2008/063181, mailed Aug. 15, 2008.
Gurevich et al., Mesolimbic Dopamine D3 Receptors and Use of Antipsychotics in Patients with Schizophrenia, A Postmortem Study, Archives of General Psychiatry, 54, 225-232, 1997. Abstract.

* cited by examiner

*Primary Examiner*—James O Wilson
*Assistant Examiner*—Erich A Leeser
(74) *Attorney, Agent, or Firm*—Charles Ryan, J.D.; Michael Ciraolo, J.D.; Hemant Khanna

(57) ABSTRACT

The present invention relates to novel solvate and crystalline forms of carbamoyl-cyclohexane derivatives and, more particularly, to novel solvate and crystalline forms of trans-1{4-[2-[4-(2,3-dichlorophenyl)-piperazin-1-yl]-ethyl]-cyclohexyl}-3,3-dimethyl-urea hydrochloride. Processes for the preparation of these forms, compositions containing these forms, and methods of use thereof are also described.

9 Claims, 12 Drawing Sheets

SOLVATE AND CRYSTALLINE FORMS OF CARBAMOYL-CYCLOHEXANE DERIVATIVES

This application claims the benefit of U.S. Provisional Application No. 60/917,383, filed May 11, 2007, the entire contents of which are hereby incorporated by reference.

FIELD OF THE INVENTION

The present invention relates to novel solvate and crystalline forms of carbamoyl-cyclohexane derivatives and, more particularly, to novel solvate and crystalline forms of trans-1{4-[2-[4-(2,3-dichlorophenyl)-piperazin-1-yl]-ethyl]-cyclohexyl}-3,3-dimethyl-urea hydrochloride. Processes for the preparation of these forms, compositions containing these forms, and methods of use thereof are also described.

BACKGROUND OF THE INVENTION

International Publication No. WO 2005/012266 discloses carbamoyl-cyclohexane derivatives that are $D_3$ and $D_2$ dopamine receptor subtype preferring ligands. WO 2005/012266 discloses that trans-1{4-[2-[4-(2,3-dichlorophenyl)-piperazin-1-yl]-ethyl]-cyclohexyl}-3,3-dimethyl-urea has a binding affinity for dopamine $D_3$ receptors ($IC_{50}$ between 1 and 10 nM) and a binding affinity for dopamine $D_2$ receptors ($IC_{50}$ between 10 and 50 nM). Thus, trans-1{4-[2-[4-(2,3-dichlorophenyl)-piperazin-1-yl]-ethyl]-cyclohexyl}-3,3-dimethyl-urea may be used as a mixed dopamine $D_3/D_2$ receptor ligand for use in the treatment of disorders which require modulation of dopamine receptor(s).

One particular carbamoyl-cyclohexane derivative disclosed in Hungarian Patent Application No. P0700339 is trans-4-{2-[4-(2,3-dichlorophenyl)-piperazin-1-yl]-ethyl}-N,N-dimethylcarbamoyl-cyclohexylamine hydrochloride, which is also known as trans-1{4-[2-[4-(2,3-dichlorophenyl)-piperazin-1-yl]-ethyl]-cyclohexyl}-3,3-dimethyl-urea hydrochloride, the structural formula for which is shown below in figure (I).

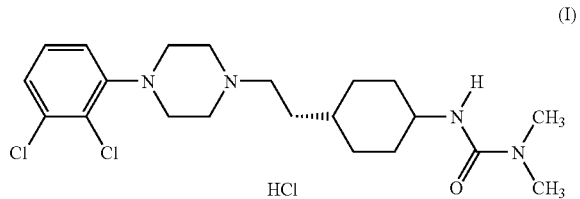

(I)

Hungarian Patent Application No. P0700339 discloses processes for preparing trans-1{4-[2-[4-(2,3-dichlorophenyl)-piperazin-1-yl]-ethyl]-cyclohexyl}-3,3-dimethyl-urea hydrochloride, and describes a crystalline form of trans-1{4-[2-[4-(2,3-dichlorophenyl)-piperazin-1-yl]-ethyl]-cyclohexyl}-3,3-dimethyl-urea hydrochloride, which will be referred to hereinafter as polymorph "Form I".

The present invention relates to the solid state physical properties of trans-1{4-[2-[4-(2,3-dichlorophenyl)-piperazin-1-yl]-ethyl]-cyclohexyl}-3,3-dimethyl-urea hydrochloride. These properties may be influenced by controlling the conditions under which this compound is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid may have therapeutic consequences since it imposes an upper limit on the rate at which an orally-administered active ingredient may reach the patient's bloodstream. The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular polymorphic form of a substance. The polymorphic form may give rise to thermal behavior different from that of the amorphous material or another polymorphic form. Thermal behavior is measured in the laboratory by such techniques as capillary melting point, thermogravimetric analysis (TGA) and differential scanning calorimetry (DSC) and may be used to distinguish some polymorphic forms from others. A particular polymorphic form may also give rise to distinct spectroscopic properties that may be detectable by powder X-ray diffractometry (XRPD), solid state nuclear magnetic resonance (NMR) spectrometry, Raman spectroscopy and infrared (IR) spectrometry.

In deciding which polymorph is preferable, the numerous properties of the polymorphs must be compared and the preferred polymorph chosen based on the many physical property variables. It is entirely possible that one polymorph can be preferable in some circumstances in which certain aspects, such as ease of preparation, stability, etc., are deemed to be critical. In other situations, a different polymorph may be preferred for greater solubility and/or superior pharmacokinetics.

The discovery of new polymorphic forms and solvates of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic. New polymorphic forms and solvates of trans-1{4-[2-[4-(2,3-dichlorophenyl)-piperazin-1-yl]-ethyl]-cyclohexyl}-3,3-dimethyl-urea hydrochloride have now been discovered.

SUMMARY OF THE INVENTION

The present invention relates to novel solvate and crystalline forms of carbamoyl-cyclohexane derivatives and, more particularly, to novel solvate and crystalline forms of trans-1{4-[2-[4-(2,3-dichlorophenyl)-piperazin-1-yl]-ethyl]-cyclohexyl}-3,3-dimethyl-urea hydrochloride. Processes for the preparation of these forms, compositions containing these forms, and methods of use thereof are also described.

DETAILED DESCRIPTION OF THE INVENTION

The present invention relates to novel solvate and crystalline forms of carbamoyl-cyclohexane derivatives and, more particularly, to novel solvate and crystalline forms of trans-1{4-[2-[4-(2,3-dichlorophenyl)-piperazin-1-yl]-ethyl]-cyclohexyl}-3,3-dimethyl-urea hydrochloride.

Hungarian Patent Application No. P0700339 discloses a crystalline form of trans-1{4-[2-[4-(2,3-dichlorophenyl)-piperazin-1-yl]-ethyl]-cyclohexyl}-3,3-dimethyl-urea hydrochloride which will be referred to hereinafter as polymorph "Form I".

Figure 1:
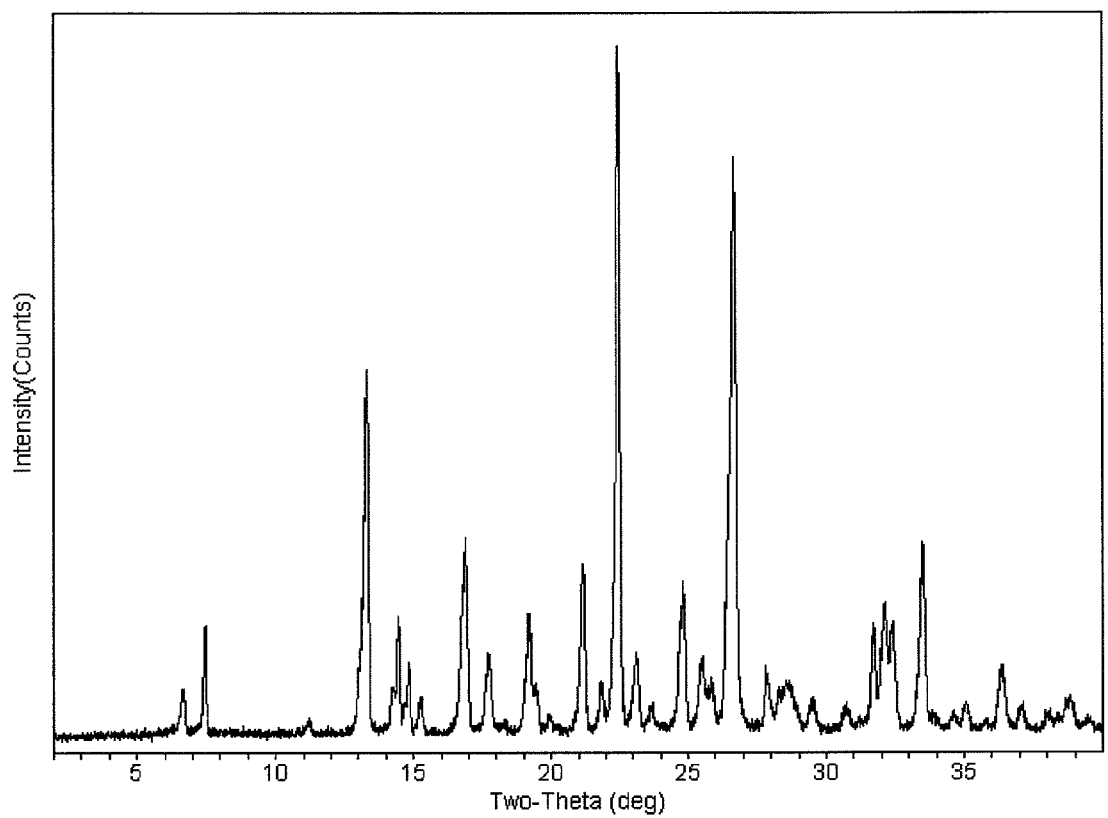
FIG. 1 shows the X-ray powder diffraction pattern of Form I trans-1{4-[2-[4-(2,3-dichlorophenyl)-piperazin-1-yl]-ethyl]-cyclohexyl}-3,3-dimethyl-urea hydrochloride.

The X-ray powder diffraction pattern of Form I is provided in FIG. 1. Form I displays a X-ray powder diffraction pattern having characteristic peaks at about 6.7, about 7.5, about 13.3, about 21.2, and about 23.1±0.2 degrees 2θ.

Figure 2:
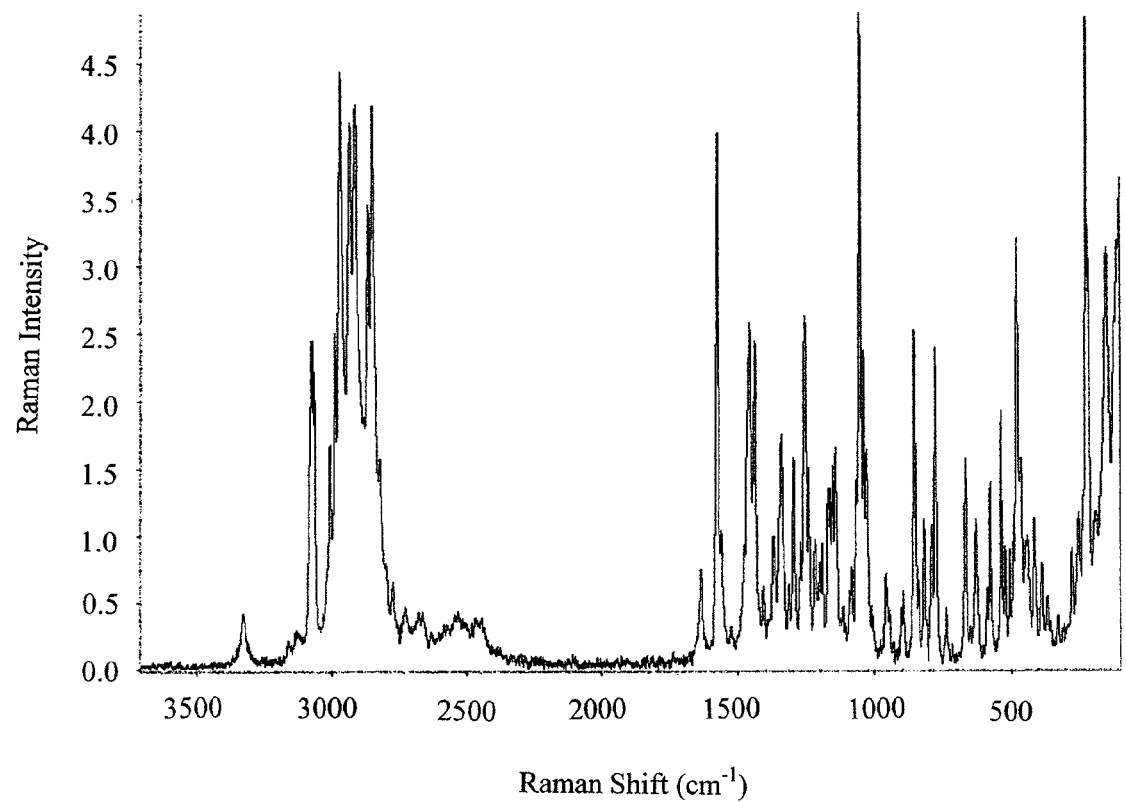
FIG. 2 shows the FT Raman spectrum for Form I trans-1{4-[2-[4-(2,3-dichlorophenyl)-piperazin-1-yl]-ethyl]-cyclohexyl}-3,3-dimethyl-urea hydrochloride.

FIG. 2 shows the FT-Raman spectrum for Form I trans-1{4-[2-[4-(2,3-dichlorophenyl)-piperazin-1-yl]-ethyl]-cyclohexyl}-3,3-dimethyl-urea hydrochloride.

Figure 3:
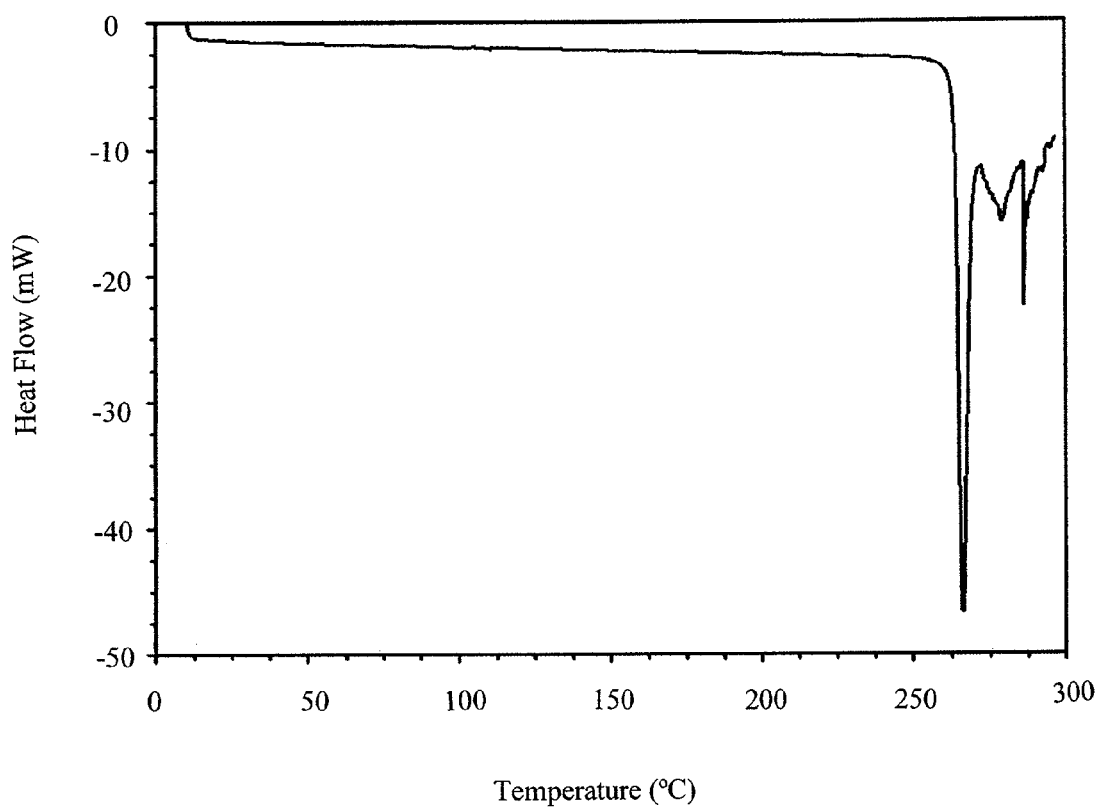
FIG. 3 shows the differential scanning calorimetry trace for Form I trans-1{4-[2-[4-(2,3-dichlorophenyl)-piperazin-1-yl]-ethyl]-cyclohexyl}-3,3-dimethyl-urea hydrochloride.

FIG. 3 shows the DSC trace for Form I trans-1{4-[2-[4-(2,3-dichlorophenyl)-piperazin-1-yl]-ethyl]-cyclohexyl}-3,3-dimethyl-urea hydrochloride.

Figure 4:
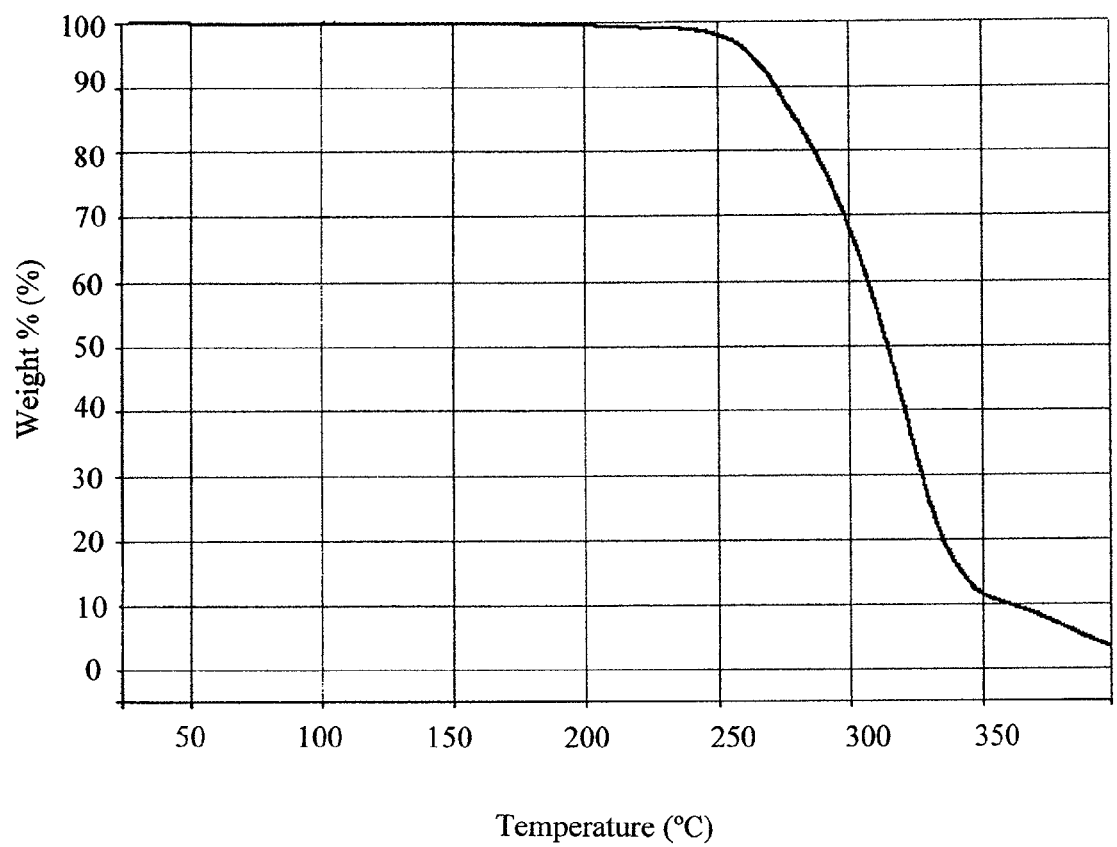
FIG. 4 shows the thermogravimetric analysis for Form I trans-1{4-[2-[4-(2,3-dichlorophenyl)-piperazin-1-yl]-ethyl]-cyclohexyl}-3,3-dimethyl-urea hydrochloride

FIG. 4 shows the thermogravimetric analysis for Form I trans-1{4-[2-[4-(2,3-dichlorophenyl)-piperazin-1-yl]-ethyl]-cyclohexyl}-3,3-dimethyl-urea hydrochloride.

Form III

The present invention provides a crystalline form of trans-1{4-[2-[4-(2,3-dichlorophenyl)-piperazin-1-yl]-ethyl]-cyclohexyl}-3,3-dimethyl-urea hydrochloride (Form III) which can be identified by one or more analytical methods. The X-ray powder diffraction pattern of Form III is provided in FIG. 5.

In one embodiment, the present invention provides a crystalline form of trans-1{4-[2-[4-(2,3-dichlorophenyl)-piperazin-1-yl]-ethyl]-cyclohexyl}-3,3-dimethyl-urea hydrochloride (Form III) characterized by a X-ray powder diffraction pattern comprising one or more characteristic peaks at about 4.1, about 12.3, about 16.5, and about 17.4±0.2 degrees 2θ. In further embodiments, the X-ray diffraction pattern comprises at least one, for example, at least two, at least three or four characteristic peaks selected from about 4.1, about 12.3, about 16.5, and about 17.4±0.2 degrees 2θ.

Figure 5:
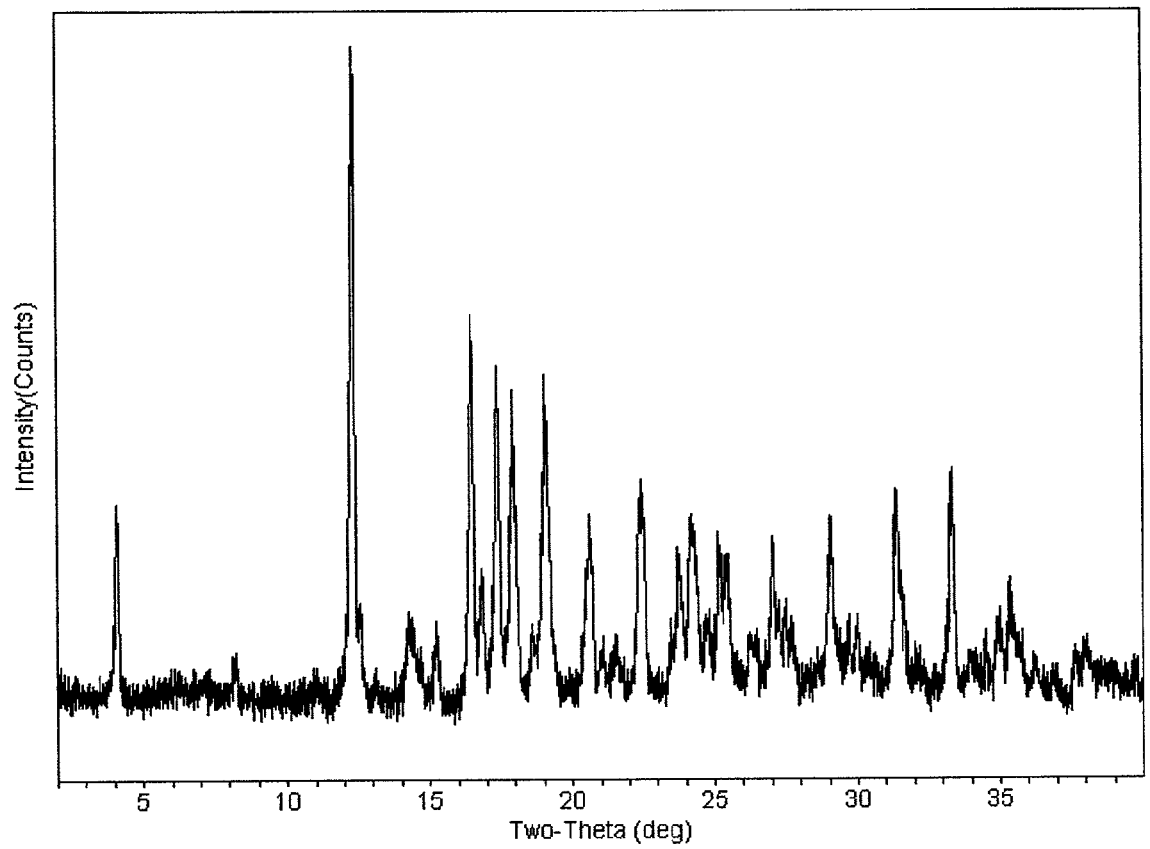
FIG. 5 shows the X-ray powder diffraction pattern of Form III trans-1{4-[2-[4-(2,3-dichlorophenyl)-piperazin-1-yl]-ethyl]-cyclohexyl}-3,3-dimethyl-urea hydrochloride.

In a further embodiment, Form III trans-1{4-[2-[4-(2,3-dichlorophenyl)-piperazin-1-yl]-ethyl]-cyclohexyl}-3,3-dimethyl-urea hydrochloride is characterized by a X-ray powder diffraction pattern substantially as shown in FIG. 5. With respect to the term "substantially," one skilled in the art would understand that the relative intensities of the peaks can vary, depending upon the sample preparation technique, the sample mounting procedure and the particular instrument employed. Moreover, instrument variation and other factors can affect the 2θ values. Therefore, the XRD peak assignments can vary by plus or minus about 0.2 degrees 2θ.

Figure 6:
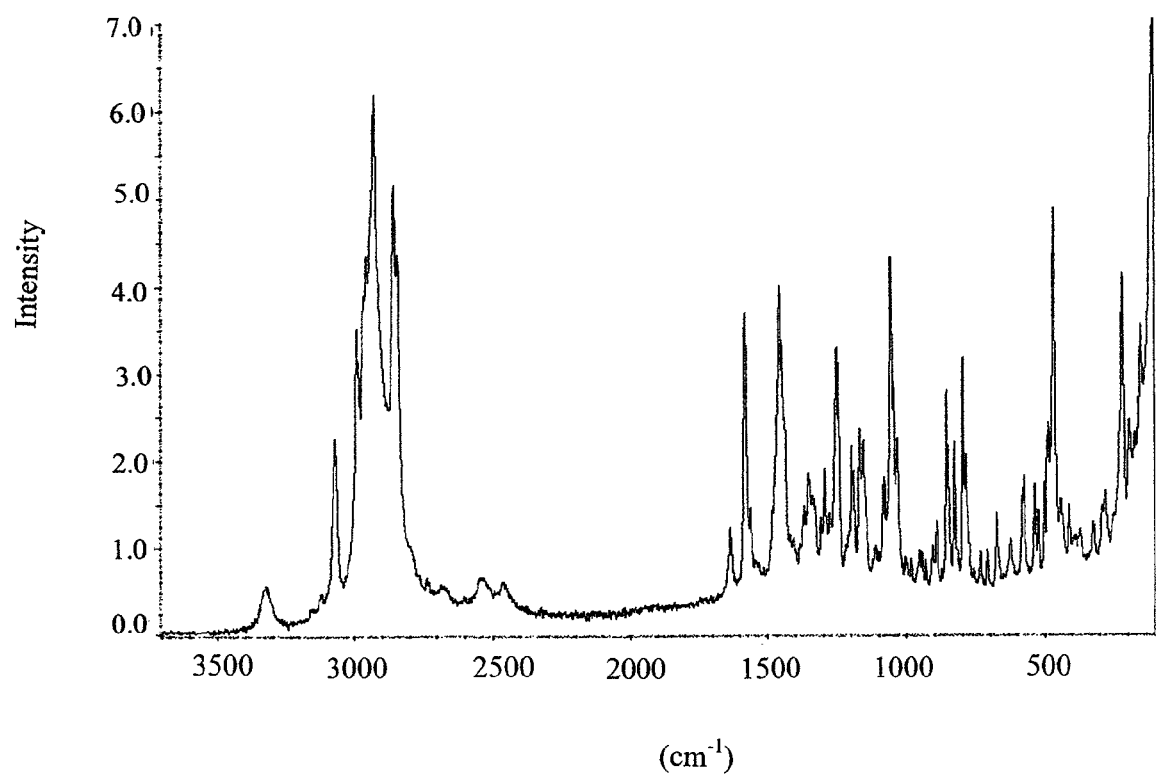
FIG. 6 shows the FT Raman Spectrum for Form III trans-1{4-[2-[4-(2,3-dichlorophenyl)-piperazin-1-yl]-ethyl]-cyclohexyl}-3,3-dimethyl-urea hydrochloride.

Form III trans-1{4-[2-[4-(2,3-dichlorophenyl)-piperazin-1-yl]-ethyl]-cyclohexyl}-3,3-dimethyl-urea hydrochloride can also be identified by its FT Raman spectrum, which is shown in FIG. 6.

Figure 7:
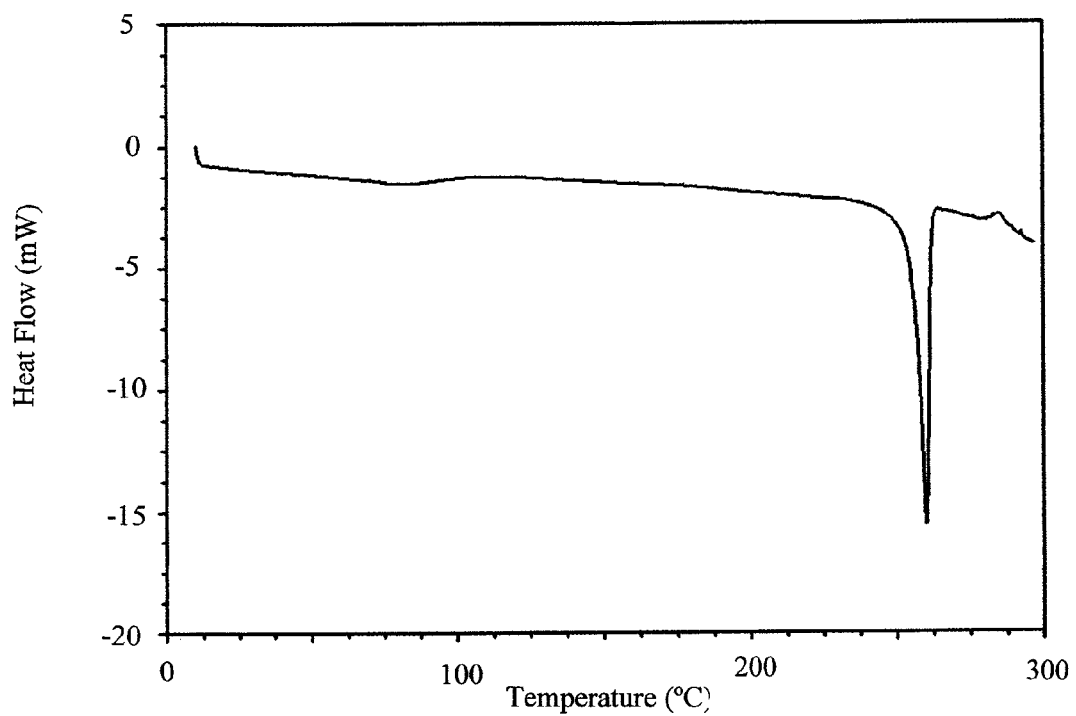
FIG. 7 shows the differential scanning calorimetry trace for Form III trans-1{4-[2-[4-(2,3-dichlorophenyl)-piperazin-1-yl]-ethyl]-cyclohexyl}-3,3-dimethyl-urea hydrochloride.

In another embodiment, Form III trans-1{4-[2-[4-(2,3-dichlorophenyl)-piperazin-1-yl]-ethyl]-cyclohexyl}-3,3-dimethyl-urea hydrochloride can also be identified by its characteristic differential scanning calorimetry (DSC) trace, such as shown in FIG. 7. In a further embodiment, Form III is characterized by a DSC trace showing a melting endotherm at about 260° C.

Figure 8:
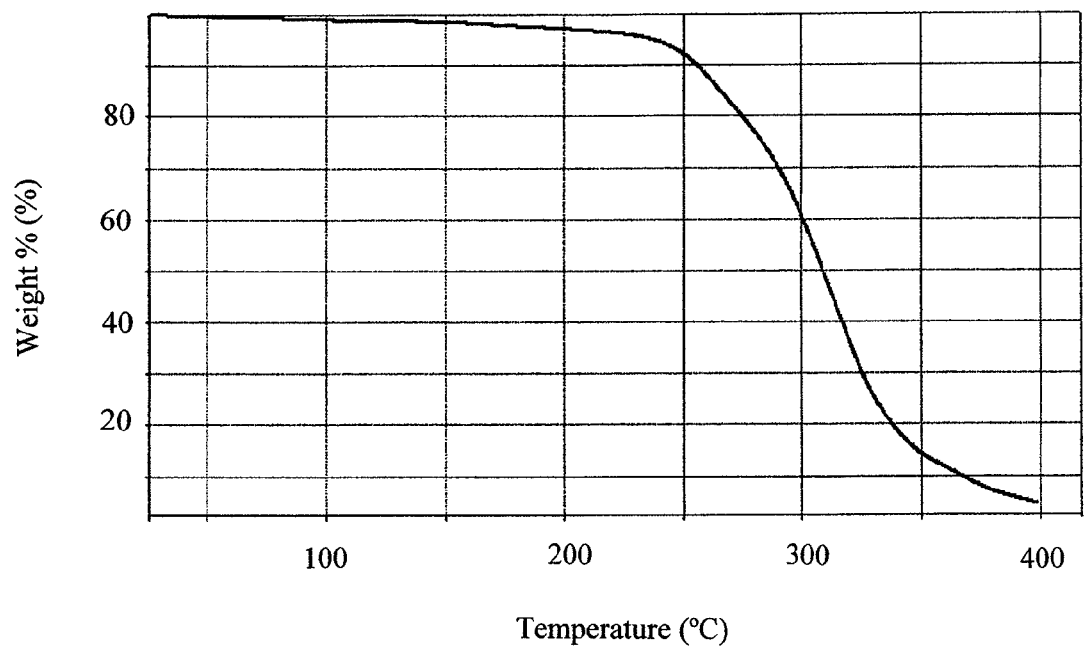
FIG. 8 shows the thermogravimetric analysis for Form III trans-1{4-[2-[4-(2,3-dichlorophenyl)-piperazin-1-yl]-ethyl]-cyclohexyl}-3,3-dimethyl-urea hydrochloride.

The thermogravimetric analysis (TGA) trace for Form III trans-1{4-[2-[4-(2,3-dichlorophenyl)-piperazin-1-yl]-ethyl]-cyclohexyl}-3,3-dimethyl-urea hydrochloride is shown in FIG. 8.

The present invention also provides processes for preparing crystalline Form III trans-1{4-[2-[4-(2,3-dichlorophenyl)-piperazin-1-yl]-ethyl]-cyclohexyl}-3,3-dimethyl-urea hydrochloride.

In one embodiment, Form III may be prepared by dissolving trans-1{4-[2-[4-(2,3-dichlorophenyl)-piperazin-1-yl]-ethyl]-cyclohexyl}-3,3-dimethyl-urea hydrochloride in pyridine to form a solution (e.g., a super-saturated solution) and crystallizing Form III from the solution.

In one embodiment, the mixture of trans-1{4-[2-[4-(2,3-dichlorophenyl)-piperazin-1-yl]-ethyl]-cyclohexyl}-3,3-dimethyl-urea hydrochloride in pyridine is heated before recrystallization. A suitable temperature, for example, is between about 30° C. and about 60° C., such as between about 40° C. and about 50° C., e.g., about 45° C.

In another embodiment, the starting material for preparation of the Form III product is Form I trans-1{4-[2-[4-(2,3-dichlorophenyl)-piperazin-1-yl]-ethyl]-cyclohexyl}-3,3-dimethyl-urea hydrochloride.

Recrystallization may occur by any of numerous routine methods in the art, such as by cooling or evaporating the solvent to induce precipitation. In one embodiment, after dissolution, crystallization is induced by cooling the mixture. For example, cooling is carried out at a temperature between about −10° C. to about 10° C. In another embodiment, crystals are obtained from a saturated solution at room temperature.

The crystal forms may be dried. For example, drying is carried out at atmospheric pressure (e.g., by allowing the solvent to evaporate), or at reduced pressure (below 1 atm), e.g., below about 100 mm Hg. For example, the drying is carried out at atmospheric pressure and room temperature.

In one embodiment, the Form III trans-1{4-[2-[4-(2,3-dichlorophenyl)-piperazin-1-yl]-ethyl]-cyclohexyl}-3,3-dimethyl-urea hydrochloride is isolated in substantially pure form.

Formic Acid Solvate

In another embodiment, the present invention provides a formic acid solvate of trans-1{4-[2-[4-(2,3-dichlorophenyl)-piperazin-1-yl]-ethyl]-cyclohexyl}-3,3-dimethyl-urea hydrochloride which can be identified by one or more analytical methods. The X-ray powder diffraction pattern of the formic acid solvate is provided in FIG. 9.

Figure 9:
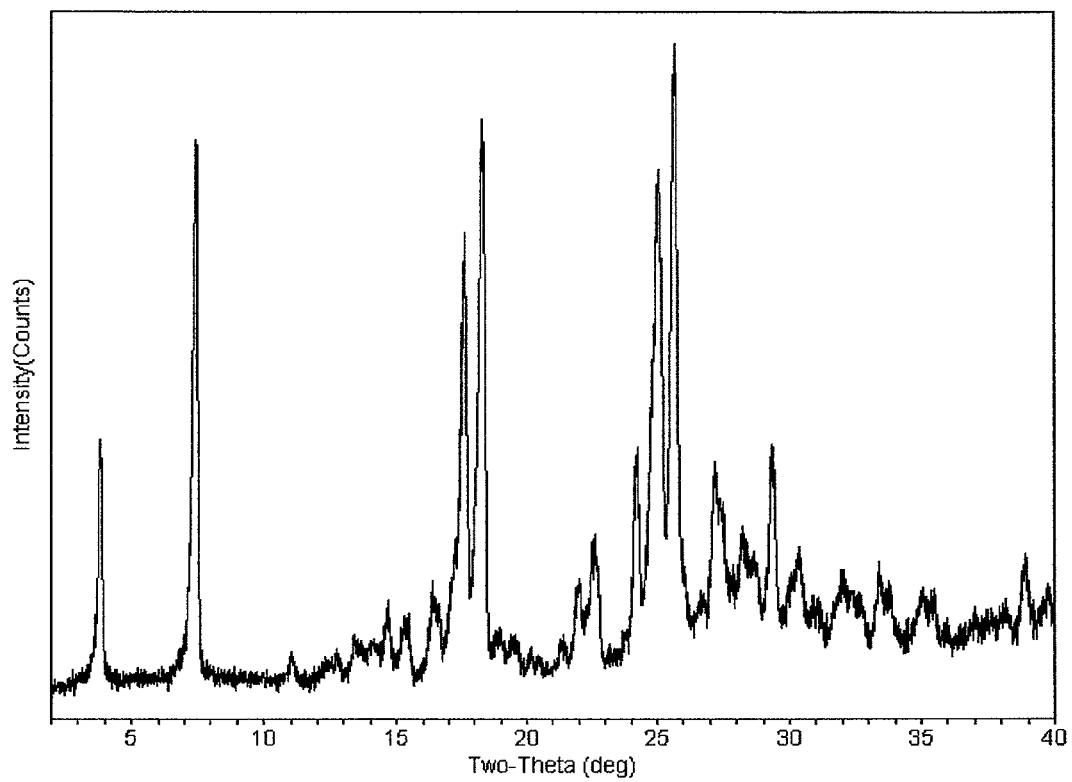
FIG. 9 shows the X-ray powder diffraction pattern of trans-1{4-[2-[4-(2,3-dichlorophenyl)-piperazin-1-yl]-ethyl]-cyclohexyl}-3,3-dimethyl-urea hydrochloride formic acid solvate.

In one embodiment, the present invention provides a formic acid solvate of trans-1{4-[2-[4-(2,3-dichlorophenyl)-piperazin-1-yl]-ethyl]-cyclohexyl}-3,3-dimethyl-urea hydrochloride characterized by a X-ray powder diffraction pattern comprising one or more characteristic peaks at about 3.8, about 7.4, about 18.3, about 24.2, and about 29.3±0.2 degrees 2θ. In further embodiments, the X-ray powder diffraction pattern comprises at least one, for example, at least two, at least three, at least four, or five characteristic peaks selected from about 3.8, about 7.4, about 18.3, about 24.2, and about 29.3±0.2 degrees 2θ. In a further embodiment, the formic acid solvate is characterized by a X-ray powder diffraction pattern substantially as shown in FIG. 9.

Figure 10:
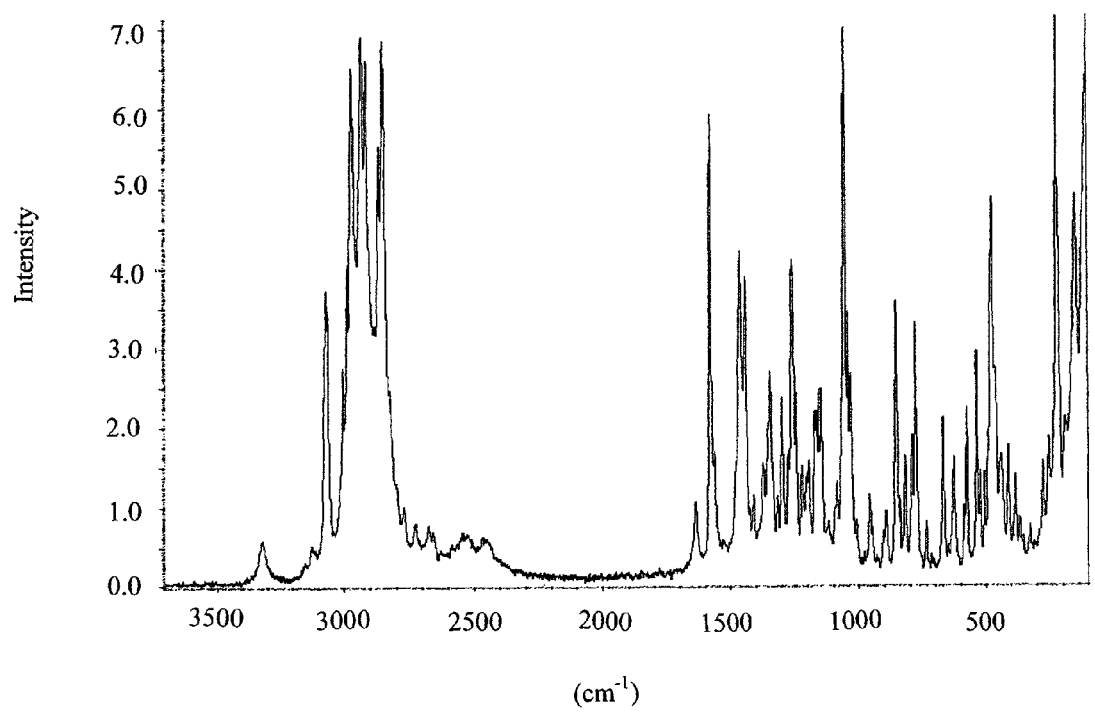
FIG. 10 shows the FT Raman Spectrum for trans-1{4-[2-[4-(2,3-dichlorophenyl)-piperazin-1-yl]-ethyl]-cyclohexyl}-3,3-dimethyl-urea hydrochloride formic acid solvate.

The formic acid solvate of trans-1{4-[2-[4-(2,3-dichlorophenyl)-piperazin-1-yl]-ethyl]-cyclohexyl}-3,3-dimethyl-urea hydrochloride can also be identified by its FT Raman spectrum, which is shown in FIG. 10.

Figure 11:
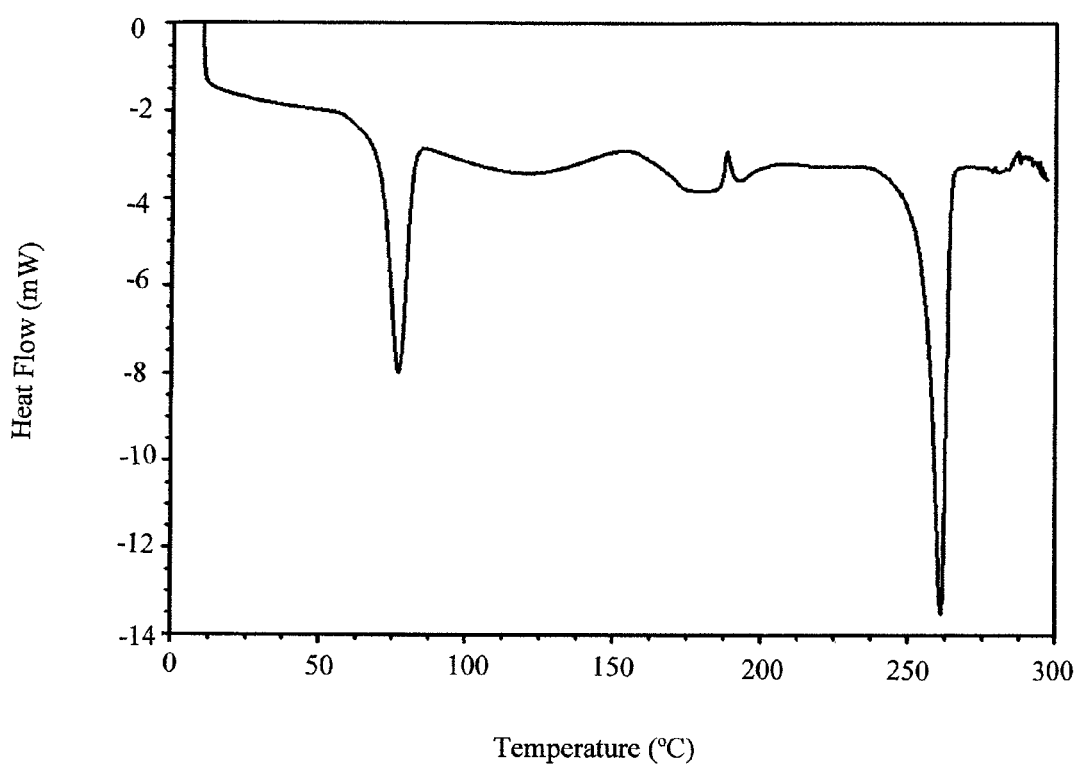
FIG. 11 shows the differential scanning calorimetry trace for trans-1{4-[2-[4-(2,3-dichlorophenyl)-piperazin-1-yl]-ethyl]-cyclohexyl}-3,3-dimethyl-urea hydrochloride formic acid solvate.

In another embodiment, the formic acid solvate can also be identified by its characteristic differential scanning calorimetry (DSC) trace, such as shown in FIG. 11. In a further embodiment, the formic acid solvate may be characterized by a DSC trace showing an endotherm at about 77° C. and a melting endotherm at about 262° C.

Figure 12:
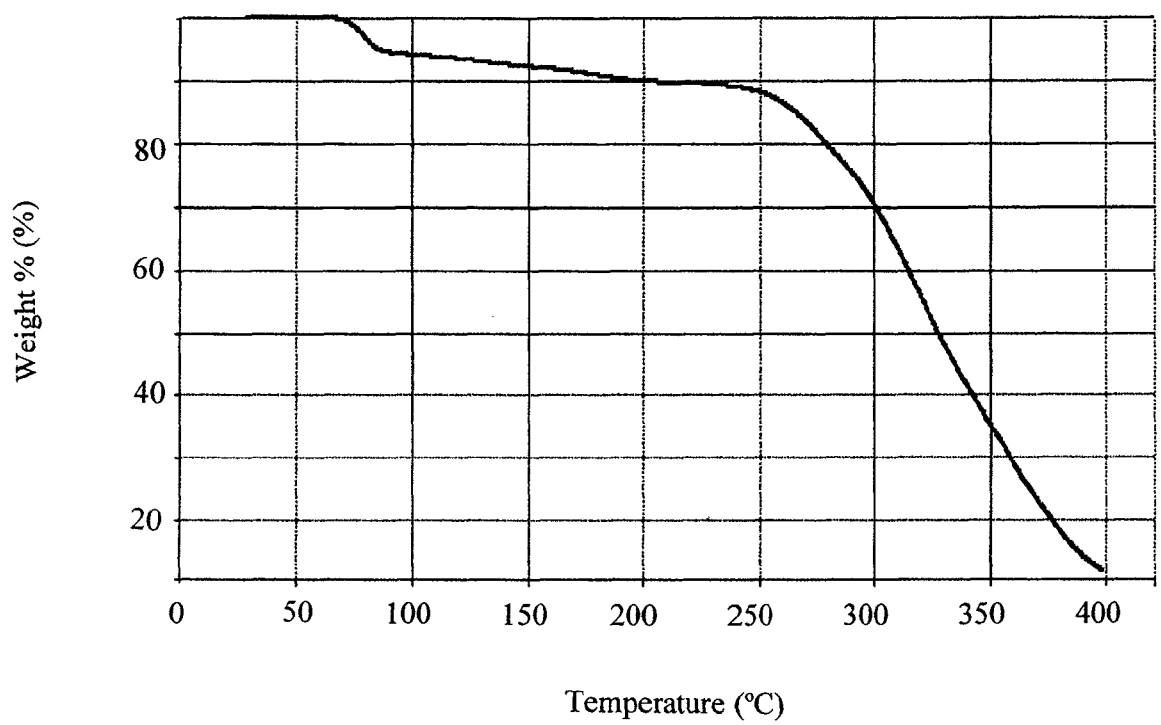
FIG. 12 shows the Thermogravimetric Analysis for trans-1{4-[2-[4-(2,3-dichlorophenyl)-piperazin-1-yl]-ethyl]-cyclohexyl}-3,3-dimethyl-urea hydrochloride formic acid solvate.

The thermogravimetric analysis (TGA) trace for the formic acid solvate is shown in FIG. 12.

The formic acid solvate may be desolvated (e.g., converted to Form I) upon heating at elevated temperatures, e.g., 90° C., for example in the solid state.

The present invention also provides processes for preparing a formic acid solvate of trans-1{4-[2-[4-(2,3-dichlorophenyl)-piperazin-1-yl]-ethyl]-cyclohexyl}-3,3-dimethyl-urea hydrochloride.

In one embodiment, the formic acid solvate may be prepared by crystallizing the formic acid solvate from a slurry of trans-1{4-[2-[4-(2,3-dichlorophenyl)-piperazin-1-yl]-ethyl]-cyclohexyl}-3,3-dimethyl-urea hydrochloride in formic acid.

In another embodiment, the starting material for preparation of the formic acid solvate is Form I trans-1{4-[2-[4-(2,3-dichlorophenyl)-piperazin-1-yl]-ethyl]-cyclohexyl}-3,3-dimethyl-urea hydrochloride.

Recrystallization may occur by any of numerous routine methods in the art, such as by cooling or evaporating the solvent to induce precipitation. In one embodiment, after dissolution, crystallization is induced by cooling the mixture. For example, cooling is carried out at a temperature between about −10° C. to about 10° C. In another embodiment, crystals are obtained from a super saturated solution at room temperature.

The crystal forms may be dried. For example, drying is carried out at atmospheric pressure (e.g., by allowing the solvent to evaporate), or at reduced pressure (below 1 atm), e.g., below about 100 mm Hg. For example, the drying is carried out at atmospheric pressure and room temperature.

One skilled in the art will understand that the relative intensities and positions of the peaks obtained by X-ray powder diffraction and bands obtained by infrared or Raman spectroscopy may vary depending upon, inter alia, the sample preparation technique, the sample mounting procedure and the particular instrument employed.

Compositions

The polymorphs and/or solvates of the invention can be administered alone or as an active ingredient of a formulation. Thus, the present invention also includes pharmaceutical compositions of polymorphs and solvates of the invention, containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

Administration of the polymorphs and solvates of the present invention may be accomplished according to patient needs, for example, orally, nasally, parenterally (subcutaneously, intravenously, intramuscularly, intrasternally and by infusion) by inhalation, rectally, vaginally, topically and by ocular administration.

Various solid oral dosage forms can be used for administering the polymorphs and solvates of the invention including such solid forms as tablets, gelcaps, capsules, caplets, granules, lozenges and bulk powders. The polymorphs and solvates of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering the polymorphs and solvates of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The polymorphs and solvates of the present invention may be injected, for example, intravenously, in the form of an isotonic sterile solution. Other preparations are also possible.

Suppositories for rectal administration of the polymorphs and solvates of the present invention can be prepared by mixing the compound with a suitable excipient such as cocoa butter, salicylates and polyethylene glycols. Formulations for vaginal administration can be in the form of a pessary, tampon, cream, gel, past foam, or spray formula containing, in addition to the active ingredient, such suitable carriers as are known in the art.

For topical administration, the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

In one embodiment, the invention provides a composition containing Form III trans-1{4-[2-[4-(2,3-dichlorophenyl)-piperazin-1-yl]-ethyl]-cyclohexyl}-3,3-dimethyl-urea hydrochloride.

In another embodiment, the invention provides a composition containing Form I trans-1{4-[2-[4-(2,3-dichlorophenyl)-piperazin-1-yl]-ethyl]-cyclohexyl}-3,3-dimethyl-urea hydrochloride and Form III trans-1{4-[2-[4-(2,3-dichlorophenyl)-piperazin-1-yl]-ethyl]-cyclohexyl}-3,3-dimethyl-urea hydrochloride.

In a further embodiment, the invention provides a composition containing a formic acid solvate of trans-1{4-[2-[4-(2,3-dichlorophenyl)-piperazin-1-yl]-ethyl]-cyclohexyl}-3,3-dimethyl-urea hydrochloride.

In a further embodiment, the invention provides a composition containing a formic acid solvate of trans-1{4-[2-[4-(2,3-dichlorophenyl)-piperazin-1-yl]-ethyl]-cyclohexyl}-3,3-dimethyl-urea hydrochloride and Form I and/or Form III trans-1{4-[2-[4-(2,3-dichlorophenyl)-piperazin-1-yl]-ethyl]-cyclohexyl}-3,3-dimethyl-urea hydrochloride.

The invention also provides the use of a compound of the present invention in the manufacture of a medicament for the treatment of conditions which require modulation of a dopamine receptor, e.g., a dopamine $D_3$ and/or $D_2$ receptor.

The present invention further provides methods for treating a condition which requires modulation of a dopamine receptor, e.g., a dopamine $D_3$ and/or $D_2$ receptor. In further embodiments, the present invention provides methods for treating a condition which requires modulation of a dopamine $D_3$ and/or $D_2$ receptor utilizing one or more compounds of the present invention.

Dysfunction of the dopaminergic neurotransmitter system is involved in the pathology of several neuropsychiatric and neurodegenerative disorders, such as schizophrenia, drug abuse and Parkinson's disease, respectively. The effect of dopamine is mediated via at least five distinct dopamine receptors belonging to the $D_1$-($D_1$, $D_5$) or the $D_2$-($D_2$, $D_3$, $D_4$) families. $D_3$ receptors have been shown to have characteristic distribution in the cerebral dopaminergic systems. Namely, high densities were found in certain limbic structures, such as nucleus accumbens and islands of Calleja. Therefore, preferential targeting of the $D_3$ receptors may be a promising approach for more selective modulation of dopaminergic functions and consequently for successful therapeutic intervention in several abnormalities, such as schizophrenia, emotional or cognitive dysfunctions and addiction (see, e.g., Sokoloff, P. et al.: *Nature,* 1990, 347, 146; Schwartz, J. C., et al.: *Clin. Neuropharmacol.* 1993, 16, 295; Levant, B.: *Pharmacol. Rev.* 1997, 49, 231), addiction (see, e.g., Pilla, C. et al.: *Nature* 1999, 400, 371) and Parkinson's disease (see, e.g., Levant, B. et al.: *CNS Drugs* 1999, 12, 391) or pain (see, e.g., Levant, B. et al.: *Neurosci. Lett.* 2001, 303, 9).

The dopamine $D_2$ receptors are widely distributed in the brain and are known to be involved in numerous physiological functions and pathological states. $D_2$ antagonists are widely used drugs as antipsychotics, for example. However, it is also well known that massive antagonism of the $D_2$ receptors leads to unwanted side-effects such as extrapyramidal motor symptoms, psychomotor sedation or cognitive disturbances. These side effects seriously restrict the therapeutic utilization of $D_2$ antagonist compounds. (Wong A. H. C. et al.: Neurosci. Biobehav. Rev. 2003, 27, 269).

In a further aspect, the present invention provides a method of treating conditions which require preferential modulation of dopamine $D_3$ and/or $D_2$ receptors, for example psychoses (e.g. schizophrenia, schizo-affective disorders), cognitive impairment accompanying schizophrenia, mild-to-moderate cognitive deficits, dementia, psychotic states associated with dementia, psychotic depression, mania, acute mania, bipolar disorder, paranoid and delusional disorders, dyskinetic disorders such as Parkinson's disease, neuroleptic induced parkinsonism, tardive dyskinesia, eating disorders (e.g. bulimia nervosa), attention deficit disorders, hyperactivity disorders in children, depression, anxiety, sexual dysfunction, sleep disorders, emesis, aggression, autism and drug abuse, which comprises administering to a subject in need thereof an effective amount of a polymorph or solvate or combinations thereof, of the present invention.

A preferred use for $D_3/D_2$ antagonists with $D_3$ preference according to the present invention is in the treatment of schizophrenia, schizo-affective disorders, cognitive impairment accompanying schizophrenia, mild-to-moderate cognitive deficits, dementia, psychotic states associated with dementia, psychotic depression, mania, acute mania, bipolar disorder, paranoid and delusional disorders, dyskinetic disorders such as Parkinson's disease, neuroleptic induced parkinsonism, depression, anxiety, drug abuse (e.g. cocaine abuse).

In one embodiment, the condition treated is schizophrenia. In embodiment, the condition treated is acute mania. In a further embodiment, the condition treated is acute mania associated with bipolar disorder.

The particular combination of the two receptor-actions described above allows the simultaneous manifestation of the beneficial actions of both the $D_3$ antagonism (e.g. cognitive enhancer effect, inhibition of extrapyramidal motor symptoms, inhibitory action on drug abuse) and the $D_2$ antagonism (e.g. antipsychotic effect). Furthermore, the same combination surprisingly results in canceling out the disadvantageous features of $D_2$ antagonism (e.g. extrapyramidal symptoms, psychomotor sedation, cognitive disturbances).

In some embodiments, the compounds of the present invention are administered as a mono-therapy. In other embodiments, the compounds of the present invention are administered as part of a combination therapy. For example, a compound of the invention may be used in combination with other drugs or therapies that are used in the treatment/prevention/suppression or amelioration of the diseases or conditions for which compounds of the invention are useful.

Such other drug(s) may be administered, by a route and in an amount commonly used therefor, contemporaneously or sequentially with a compound of the invention. When a compound of the present invention is used contemporaneously with one or more other drugs, a pharmaceutical unit dosage form containing such other drugs in addition to the compound of the invention may be employed. Accordingly, the pharmaceutical compositions of the present invention include those that also contain one or more other active ingredients, in addition to a compound of invention.

The compounds of the present invention can normally be administered in a daily dosage regimen (for an adult patient) of, for example, an oral dose between 1 mg and 500 mg, such as between 10 mg and 400 mg, e.g. between 10 mg and 250 mg or an intravenous, subcutaneous, or intramuscular dose of between 0.1 mg and 100 mg, such as between 0.1 mg and 50 mg, e.g. between 1 and 25 mg of the compound of present invention.

In certain embodiments, the active ingredient is administered in an amount of about 0.05 mg, about 0.1 mg, about 0.2 mg, about 0.3 mg, about 0.4 mg, about 0.5 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg or about 15 mg. For example, the active ingredient is administered in an amount of about 0.5 mg, about 1.0 mg, about 1.5 mg, about 2 mg, about 2.5 mg, about 3 mg, about 3.5 mg, about 4 mg, about 4.5 mg, about 5 mg or about 6 mg. In exemplary embodiments, the active ingredient is administered in an amount of about 1.5 mg, about 3 mg or about 4.5 mg. In yet further embodiments, the active ingredient is administered in an amount which ranges between any two of these dosage amounts. For example, the active ingredient is administered in an amount ranging from about 0.5 mg to about 12 mg, from about 0.5 mg to about 6 mg, from about 1 mg to about 6 mg. In an exemplary embodiment, the active ingredient is administered in an amount ranging from about 1.5 mg to about 4.5 mg.

The compounds of the present invention can be administered 1 to 4 times per day, for example, once a day, twice a day. The compounds of the present invention can suitably be administered for a period of continuous therapy, for example for a week or more.

Subjects suffering from and in need of treatment of, e.g., schizophrenia, acute mania, and the other conditions mentioned above can be treated by the administering a therapeutically effective amount of Form III trans-1{4-[2-[4-(2,3-dichlorophenyl)-piperazin-1-yl]-ethyl]-cyclohexyl}-3,3-dimethyl-urea hydrochloride (optionally with one or more other form(s) of trans-1{4-[2-[4-(2,3-dichlorophenyl)-piperazin-1-yl]-ethyl]-cyclohexyl}-3,3-dimethyl-urea hydrochloride, such as, for example, Form I trans-1{4-[2-[4-(2,3-dichlorophenyl)-piperazin-1-yl]-ethyl]-cyclohexyl}-3,3-dimethyl-urea hydrochloride) formulated according to, for example and without limitation, the compositions and dosage forms described herein.

Subjects suffering from and in need of treatment of, e.g., schizophrenia, acute mania, and the other conditions mentioned above can be treated by the administering a therapeutically effective amount of a formic acid solvate of trans-1{4-[2-[4-(2,3-dichlorophenyl)-piperazin-1-yl]-ethyl]-cyclohexyl}-3,3-dimethyl-urea hydrochloride (optionally with one or more other form(s) of trans-1{4-[2-[4-(2,3-dichlorophenyl)-piperazin-1-yl]-ethyl]-cyclohexyl}-3,3-dimethyl-urea hydrochloride, such as, for example, Form I and/or Form III trans-1{4-[2-[4-(2,3-dichlorophenyl)-piperazin-1-yl]-ethyl]-cyclohexyl}-3,3-dimethyl-urea hydrochloride) formulated according to, for example and without limitation, the compositions and dosage forms described herein.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value.

The term "substantially pure" means a compound having a purity greater then, e.g., about 90% by weight, for example, greater than about 91% by weight, greater than about 92% by weight, greater than about 93% by weight, greater than about 94% by weight, greater than about 95% by weight, greater than about 96% by weight, greater than about 97% by weight, greater than about 97.5% by weight, greater than about 98% by weight, greater than about 99% by weight, greater than about 99.5% by weight, or greater than about 99.9% by weight.

The term "treating" means to relieve, alleviate, delay, reduce, reverse, improve or prevent at least one symptom of a condition in a subject. The term "treating" may also mean to arrest, delay the onset (i.e., the period prior to clinical manifestation of a disease) and/or reduce the risk of developing or worsening a condition.

An "effective amount" means the amount of a solvate or polymorph of the present invention that, when administered to a patient (e.g., a mammal) for treating a disease, is sufficient to effect such treatment for the disease, or an amount of a compound that is sufficient for modulating a dopamine receptor (e.g., the dopamine $D_2$ and/or dopamine $D_3$ receptor) to achieve the objectives of the invention. The "effective amount" will vary depending on the compound, the disease and its severity and the age, weight, etc., of the patient to be treated.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The following examples are merely illustrative of the present invention and should not be construed as limiting the scope of the invention in any way as many variations and equivalents that are encompassed by the present invention will become apparent to those skilled in the art upon reading the present disclosure.

EXAMPLES

X-Ray Powder Diffraction (XRD) Analysis

A small amount of sample (~12 mg) was loaded on a zero background holder and exposed to CuKα radiation (30 kV×15 mA) in a wide-angle bench-top X-ray diffractometer (Model MiniFlex, Rigaku/MSC Inc., Woodlands, Tex.). The instrument was operated in the step-scan mode, in increments of 0.05° 2θ. The angular range was 2 to 40° 2θ, and the scan rates ranged from 1.0-3.0° 2θ/min. The data collection and analyses were performed using commercially available software (JADE, version 7.1, Materials Data, Inc., Livermore, Calif.).

Fourier Transform Raman Spectroscopy (FT-Raman).

A small amount of sample (~5 mg) was loaded on a glass slide and exposed to Raman laser in a Raman spectrophotometer (Thermo Nicolet Nexus 670 FT-IR/FT-Raman spectrometer, Thermo Electron, Waltham Mass.) using Nicolet EZ Omnic 5.1 software. All spectra were run at 3600-100 cm$^{-1}$ stokes shift, 100 scans and 2 cm$^{-1}$ resolution.

Differential Scanning Calorimetry (DSC)

A differential scanning calorimeter (MDSC Q1000, TA Instruments, New Castle, Del.) with a refrigerated cooling accessory was used. The instrument was calibrated with pure samples of indium. About 3-5 mg sample was weighed in open aluminum pans and heated under dry nitrogen purge (flow rate 50 ml/min) at 10° C./min. The data was analyzed using Universal Analysis 2000 (TA instruments, New Castle, Del.).

Thermogravimetric Analysis (TGA)

A Thermogravimetric analyzer (Pyris 1, Perkin Elmer, Wellesley, Mass.) with air cooling was used. About 3~7 mg sample was weighed in platinum TGA pans and heated under dry nitrogen purge (flow rate 70 ml/min) at 10° C./min. The data was analyzed using Pyris software (version 5.00.02, Perkin Elmer, Wellesley, Mass.).

Trans-1{4-[2-[4-(2,3-dichlorophenyl)-piperazin-1-yl]-ethyl]-cyclohexyl}-3,3-dimethyl-urea hydrochloride Form I was prepared as described in Hungarian Patent Application No. P0700339.

General Experimental Procedure

Trans-1{4-[2-[4-(2,3-dichlorophenyl)-piperazin-1-yl]-ethyl]-cyclohexyl}-3,3-dimethyl-urea hydrochloride was crystallized using a variety of solvents under three conditions:

(i) recrystallization from a saturated solution at room temperature, (ii) recrystallization from a saturated solution at approximately 45° C. to 50° C., or (iii) recrystallization from a slurry, i.e., from a supersaturated solution with undissolved trans-1{4-[2-[4-(2,3-dichlorophenyl)-piperazin-1-yl]-ethyl]-cyclohexyl}-3,3-dimethyl-urea hydrochloride present.

In order to obtain different samples from one set of sample preparation, the following preparation method was utilized.

A weighed amount of Form I trans-1{4-[2-[4-(2,3-dichlorophenyl)-piperazin-1-yl]-ethyl]-cyclohexyl}-3,3-dimethyl-urea hydrochloride was dispersed in a constant volume of a particular solvent at 25° C. in a glass test tube, which was then capped and sonicated for 2 hours. One third of this sample was removed, filtered through a syringeless filter and transferred to a well plate for recrystallization (condition (i)). The remaining sample was further sonicated/shaken in a water bath at approximately 45° C. for two hours. Half of the remaining sample was filtered and transferred to a well plate for recrystallization (condition (ii)). The remaining slurry was left unchanged in the test tube (condition (iii)). During the process, if at any point the entire starting material dissolved in the solvent more Form I trans-1{4-[2-[4-(2,3-dichlorophenyl)-piperazin-1-yl]-ethyl]-cyclohexyl}-3,3-dimethyl-urea hydrochloride was added to maintain saturation.

Recrystallizations were conducted at room temperature, and the recrystallized samples were dried under ambient conditions.

Example 1

Preparation of Form III trans-1{4-[2-[4-(2,3-dichlorophenyl)-piperazin-1-yl]-ethyl]-cyclohexyl}-3,3-dimethyl-urea hydrochloride Form III trans-1{4-[2-[4-(2,3-dichlorophenyl)-piperazin-1-yl]-ethyl]-cyclohexyl}-3,3-dimethyl-urea hydrochloride was prepared using the above general procedure, using pyridine as the solvent, and the product was isolated from a sample according to condition (ii).

Example 2

Preparation of trans-1{4-[2-[4-(2,3-dichlorophenyl)-piperazin-1-yl]-ethyl]-cyclohexyl}-3,3-dimethyl-urea hydrochloride formic acid solvate Trans-1{4-[2-[4-(2,3-dichlorophenyl)-piperazin-1-yl]-ethyl]-cyclohexyl}-3,3-dimethyl-urea hydrochloride formic acid solvate was prepared using the above general procedure, using formic acid as the solvent, and the product was isolated from a sample according to condition (iii).

Peak locations for the XRPD patterns in FIG. 5 (Form III) and FIG. 9 (formic acid solvate) are provided in Table 1

TABLE 1

| Form III | | | Formic Acid Solvate | | |
|---|---|---|---|---|---|
| 2θ (°) | d-spacing (Å) | Relative Intensity | 2θ (°) | d-spacing (Å) | Relative Intensity |
| 4.11 | 21.480 | 23.4 | 3.86 | 22.872 | 33.8 |
| 10.27 | 8.608 | 1.2 | 7.47 | 11.825 | 83.3 |
| 10.58 | 8.359 | 3.5 | 11.06 | 7.993 | 5.8 |
| 11.04 | 8.011 | 4.7 | 12.76 | 6.933 | 5.2 |
| 12.34 | 7.167 | 100.0 | 13.45 | 6.578 | 6.0 |
| 12.60 | 7.019 | 28.8 | 14.07 | 6.289 | 7.0 |
| 14.32 | 6.180 | 19.9 | 14.70 | 6.021 | 6.0 |
| 14.71 | 6.017 | 10.1 | 15.50 | 5.712 | 9.2 |
| 15.28 | 5.795 | 6.0 | 16.40 | 5.400 | 11.7 |
| 16.50 | 5.368 | 51.0 | 17.24 | 5.139 | 14.8 |
| 16.85 | 5.257 | 14.2 | 17.64 | 5.024 | 100.0 |
| 17.41 | 5.090 | 45.7 | 18.33 | 4.836 | 99.8 |
| 17.97 | 4.932 | 45.3 | 18.97 | 4.674 | 3.9 |
| 18.63 | 4.759 | 10.5 | 19.59 | 4.527 | 3.4 |
| 19.13 | 4.636 | 58.6 | 20.18 | 4.397 | 2.6 |
| 20.64 | 4.300 | 33.9 | 20.47 | 4.335 | 1.9 |
| 21.10 | 4.207 | 8.2 | 21.33 | 4.162 | 2.6 |
| 21.55 | 4.120 | 6.4 | 22.01 | 4.035 | 23.7 |
| 21.86 | 4.063 | 3.4 | 22.63 | 3.926 | 32.1 |
| 22.49 | 3.950 | 44.1 | 24.28 | 3.663 | 35.8 |
| 23.77 | 3.740 | 23.4 | 25.07 | 3.549 | 97.2 |
| 24.24 | 3.669 | 37.5 | 25.72 | 3.461 | 75.8 |
| 24.85 | 3.581 | 3.7 | 26.77 | 3.327 | 2.7 |
| 25.17 | 3.535 | 16.5 | 27.23 | 3.272 | 34.6 |
| 25.47 | 3.495 | 17.8 | 27.51 | 3.240 | 25.2 |
| 26.25 | 3.392 | 6.4 | 27.92 | 3.193 | 1.9 |
| 26.47 | 3.365 | 6.4 | 28.24 | 3.158 | 18.1 |
| 27.03 | 3.296 | 30.1 | 28.71 | 3.107 | 9.2 |
| 27.51 | 3.240 | 14.3 | 29.35 | 3.041 | 24.2 |
| 27.71 | 3.217 | 11.6 | 30.06 | 2.970 | 13.1 |
| 29.08 | 3.068 | 24.7 | 30.40 | 2.938 | 17.7 |
| 29.70 | 3.005 | 7.5 | 30.93 | 2.889 | 2.4 |
| 30.02 | 2.974 | 4.8 | 32.07 | 2.789 | 27.2 |
| 30.41 | 2.937 | 1.6 | 32.39 | 2.762 | 22.9 |
| 31.39 | 2.848 | 35.3 | 32.74 | 2.733 | 10.5 |
| 31.68 | 2.822 | 13.7 | 33.47 | 2.675 | 14.9 |
| 32.20 | 2.778 | 3.7 | 33.83 | 2.648 | 13.8 |
| 32.37 | 2.763 | 1.6 | 35.07 | 2.557 | 13.5 |
| 32.74 | 2.733 | 1.4 | 35.51 | 2.526 | 11.4 |
| 33.38 | 2.682 | 33.7 | 36.01 | 2.492 | 1.2 |
| 33.98 | 2.636 | 4.1 | 37.04 | 2.425 | 2.6 |
| 34.52 | 2.596 | 1.9 | 37.52 | 2.395 | 4.6 |

TABLE 1-continued

| | Form III | | | Formic Acid Solvate | |
|---|---|---|---|---|---|
| 2θ (°) | d-spacing (Å) | Relative Intensity | 2θ (°) | d-spacing (Å) | Relative Intensity |
| 34.93 | 2.567 | 9.8 | 37.69 | 2.385 | 6.0 |
| 35.40 | 2.534 | 25.8 | 38.23 | 2.352 | 3.9 |
| 35.80 | 2.506 | 8.5 | 38.92 | 2.312 | 12.4 |
| 36.24 | 2.477 | 6.8 | | | |
| 36.84 | 2.438 | 3.2 | | | |
| 37.65 | 2.387 | 7.4 | | | |
| 38.05 | 2.363 | 19.9 | | | |

While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts having the benefit of this disclosure.

The depicted and described embodiments of the invention are exemplary only, and are not exhaustive of the scope of the invention. Consequently, the invention is intended to be limited only by the spirit and scope of the appended claims, giving full cognizance to equivalence in all respects.

All references cited herein are hereby incorporated by reference in their entirety.

What is claimed is:

1. A crystalline form of trans-1 {4-[2-[4-(2,3-dichlorophenyl)-piperazin-1-yl]-ethyl]-cyclohexyl}-3,3-dimethyl-urea hydrochloride (Form III) having a X-ray powder diffraction pattern comprising characteristic peaks at about 4.1, about 12.3, about 16.5, and about 17.4±0.2 degrees 2θ.

2. The crystalline form of claim 1, having a melting endotherm at about 260° C. as determined by DSC.

3. A process for preparing the crystalline form of claim 1, comprising:
   (i) adding trans-1 {4-[2-[4-(2,3-dichlorophenyl)-piperazin-1-yl]-ethyl]-cyclohexyl}-3,3-dimethyl-urea hydrochloride to pyridine; and
   (ii) precipitating the crystalline form from the solution.

4. The process of claim 3, wherein the mixture in step (i) is heated to a temperature of about 30° C. to about 50° C.

5. The process of claim 3, wherein step (i) comprises forming a saturated solution.

6. The process of claim 3, further comprising (iii) recovering the crystalline form.

7. The process of claim 6, wherein step (iii) comprises (a) filtering the precipitate formed in step (ii) and (b) drying the crystalline form.

8. A pharmaceutical composition comprising the crystalline form of claim 1.

9. The crystalline form of claim 1, having a melting endotherm at about 260° C. as determined by DSC and a characteristic peak at about 4.1±0.2 degrees 2θ in an X-ray powder diffraction pattern.

* * * * *